United States Patent [19]
Böhnensieker

[11] 4,118,191
[45] Oct. 3, 1978

[54] GAS STERILIZATION APPARATUS

[76] Inventor: Franz Böhnensieker, Vom-Stein-Strasse 22, D-4834 Harsewinkel, Germany

[21] Appl. No.: 790,102

[22] Filed: Apr. 22, 1977

[30] Foreign Application Priority Data

Apr. 26, 1976 [DE] Fed. Rep. of Germany ....... 2618127

[51] Int. Cl.² .......................... A61L 3/00; A61L 9/00; F24F 3/16
[52] U.S. Cl. ............................... 55/279; 55/DIG. 16; 422/121
[58] Field of Search ............ 21/DIG. 2, 54 R, 102 R, 21/74 R; 350/1; 250/432–438, 455, 373; 55/DIG. 16, 523, 524, 527, 279

[56] References Cited
U.S. PATENT DOCUMENTS

| | | | |
|---|---|---|---|
| 2,183,498 | 12/1939 | Anderson | 21/DIG. 2 |
| 2,941,265 | 6/1960 | Isenberg et al. | 55/279 |
| 2,968,719 | 1/1961 | Häberle et al. | 55/279 |
| 3,072,978 | 1/1963 | Minto | 55/279 |
| 3,217,470 | 11/1965 | Omohundro | 55/279 |
| 3,433,949 | 3/1969 | Truhan | 250/455 |
| 3,744,216 | 7/1973 | Halloran | 21/DIG. 2 |
| 3,881,896 | 5/1975 | Rothmayr et al. | 55/279 |

FOREIGN PATENT DOCUMENTS

| | | | |
|---|---|---|---|
| 2,333,465 | 1/1975 | Fed. Rep. of Germany | 21/74 R |
| 2,063,762 | 3/1975 | Fed. Rep. of Germany | |
| 2,461,290 | 7/1976 | Fed. Rep. of Germany | 21/54 R |

Primary Examiner—Morris O. Wolk
Assistant Examiner—Bradley Garris
Attorney, Agent, or Firm—Sughrue, Rothwell, Mion, Zinn and Macpeak

[57] ABSTRACT

Apparatus for the sterilization of gases, which can be associated with facilities for the distribution or circulation of air or with air-conditioning plant, for example. Instead of employing conventional technology based upon filtration techniques, in which harmful components such as germs are filtered out and attempts are made to kill them on the surfaces of filter elements, media-pervious materials are arranged so that germs and other harmful components carried in the gases are forced through the materials with a residence time sufficient to ensure substantially complete killing by means of UV-radiation directed at the materials. The preferred media-pervious material is a porous form of quartz.

6 Claims, 4 Drawing Figures

GAS STERILIZATION APPARATUS

BACKGROUND OF THE INVENTION

The invention relates to an apparatus for the sterilization of gaseous media, for example air, in which germs such as bacteria and the like are contained, having at least one housing frame, at least one layer having a labyrinth-like structure pervious to the medium held in the frame and at least one UV-source arranged to act upon the layer.

Such devices are installed in hospitals, medical treatment rooms and in part also in industrial locations, in order to create in the rooms in question an environmental condition which is as germ-free as possible. Conventional sterilization devices are in use, the essential component of which is a filter of a germ-impervious material, so that the germs contained in the medium are retained, but nevertheless they are not killed. There is thus a risk of penetration through the germ-proof filter material because of the continuous formation of new germs, so that such filters must be frequently replaced. During the replacement operation and also during use of the apparatus, it is therefore not possible to preclude the entry of germs into the area which is intended to be kept germ-free.

From German Offenlegungsschrift No. 2243223, it is also known to locate upstream of such a filter one or more UV-sources which have the purpose of killing the collected germs and thus preventing them from penetrating through the filter. Because of the filter materials conventionally used, the UV-radiation can effect its germ-killing action substantially only on the free filter surface, whereas it is prevented from entering inside the filter by absorption of the radiation. Because of the relatively short time during which the germs are subjected to the UV-radiation at the filter surface, it is impossible to avoid not only dead but also still living germs from passing inside the filter. During the time of use, a radiation-absorbing layer of collected germs and other retained particles forms on the free filter surface, so that the germ-killing effect of the UV-radiation at the filter surface becomes lost more or less rapidly. Like the abovementioned filters, therefore, even with the provision of UV-radiation, frequent replacement of filters, due to the disadvantages connected with the presence of living germs, is absolutely essential.

SUMMARY OF THE INVENTION

In contrast, the invention is based upon the purpose of providing a germ-killing apparatus of the construction mentioned initially, which affords an extended period of operational effectiveness together with an assurance of complete killing of the germs.

This purpose is met, in accordance with the invention, in that the layer of filter-like material non-absorbent of UV-radiation has such a labyrinth-like structure that the passage of germs through the layer is substantially not prevented, but only takes place considerably delayed, and that a blower or compressor is provided in order to force the medium to be sterilized into the layer.

In contrast to the basically germ-proof or germ-impervious filters used up till now, the invention makes use of a material for the layer which is penetrated practically loss-free by the UV-radiation. A suitable material is, for instance, quartz, which can be provided for forming the layer in the form of quartz wool, quartz paper or sintered quarts dust. The UV-radiation can thus have its effect equally at the surface of the layer and also inside it. In accordance with the invention, the layer has such a labyrinth-like construction or formation that the passage of germs through the layer in contrast to the filters previously used occurs substantially only with considerable delay, though the germs fundamentally are not prevented from passing through the layer. Moreover, the provision of a blower or compressor on the upstream side of the layer ensures that the germs are forced through the layer. Because of the labyrinth-like structure of the layer, the germ-killing effect of the UV-radiation at the inside is even higher than on the surface, since the labyrinth-like passage of the germs through the layer considerably enlarges the residence time during which the germs are subjected to the radiation. Thus the layer essentially only has the purpose of so causing multiple deflection of the germs during their passage through the layer so that a residence time is provided which ensures that only dead germs are discharged from the layer. Since there is a close relationship between the UV-radiation intensity and the residence time, in accordance with the invention, one or more UV sources are preferably provided, which are located before and/or behind and/or in the layer or also in any combination of such positions, with relatively low loadings, when the layer is correspondingly dimensioned. A substantial advantage of the invention is, furthermore, the considerably extended operational time, since the main part of the dead germs are not retained, as with filters of conventional construction, but are allowed through so that the layer remains substantially free.

According to a further feature of the invention, the layer can be made in a substantially flat form. Practice has shown however that under certain circumstances layers formed, for example, of quartz wool can include passages which extend directly from one surface to the other. It is thus preferable, in accordance with the invention, for the layer to be made with a zig-zag configuration. This ensures that the medium or the germs contained in it always contact the surface of the layer at a certain angle and thus cannot pass directly through such passageways. Moreover, the throughput cross-section as well as the germ-killing volume of the layer are substantially increased by this.

Another preferred feature of the invention is characterised in that, in a substantially parallel arrangement to the one layer, at least one further layer of material non-absorbent of UV-radiation is arranged in the frame.

Preferably, one or more UV-emitters is/are arranged in the space between the two layers so that both layers are uniformly irradiated with the UV-radiation. If desired, additional UV-emitters can also be embedded in the layers themselves. This arrangement offers the advantage, together with increased effectiveness, that thinner layers and/or those with a more open structure can be provided, whereby the deposition of dust particles and other impurities possibly contained in the medium passing through is prevented.

A separate frame can be provided for each layer and for the UV-emitter(s) or other UV-source. The frames or housings are so arranged and interrelated that they can readily be combined into an apparatus or device of the above-mentioned construction. Each layer and UV-emitter can also be held in a common frame or housing, whereby a unit ready for installation is provided.

The apparatus according to the invention is preferably installed as an air-supply or air-circulating apparatus. The apparatus can also be readily combined with air-conditioning plant, where the compressor or blower operates as a pressure increase stage, in order to raise the generally insufficient static pressure of the air-conditioning plant to a value which enhances the operational effectiveness of the apparatus.

In order to filter out from the incoming air dust particles and the like which could adversely affect the germ-killing action of the UV-radiation, in accordance with a further feature of the aerating or air-circulating apparatus according to the invention, the compressor or blower is located between a pre-filter known per se and the apparatus and deflector plates are provided, in order to direct the air extracted by the blower through the pre-filter substantially unformly into the apparatus.

A germ-killing device is thus provided in accordance with the invention, viewed as a whole, which is based upon a layer with a labyrinth-like structure of a material which over its whole cross-section fully allows the germ-killing effect of UV-radiation to take place and therefore offers a very high degree of safety that neither during the actual period of use of the device nor in any requisite replacement operation is there any serious risk that undesirable germs will get into the areas which are to be kept sterile, such as intensive care units in hospitals, operation theatres and the like.

DETAILED DESCRIPTION OF THE DRAWINGS

Figure 1:
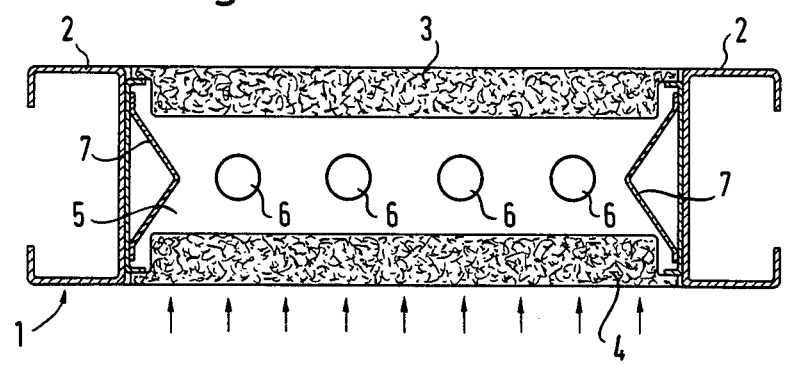
FIG. 1 shows a diagrammatic sectional view of a first embodiment of a combination of UV-emitters and layers of non-UV-absorbing material arranged as a constructional unit, for a device according to the invention.

The embodiment of the invention according to FIG. 1 includes a housing or frame 1, with a pair of spaced parallel lateral frame members 2 and, if required, upper and lower frame members (not shown). The lateral frame members 2, as shown, preferably have a substantially U-shaped outwardly-open channel cross-section and serve for securing the device in or on an air-outlet opening, not shown, for example from an air-circulating device or the like. For this purpose, guide rails can be provided on the side walls of the air outlet opening over which the device is so located from above that the lateral housing parts 2 engage the rails. If desired, the rails can be connected e.g. by means of a screw arrangement with the lateral frame parts 2, preferably using a suitable sealing material. The housing or frame 1 can consist of any suitable material, such as metal or plastics material.

Between the lateral housing parts 2 and held by them, layers 3,4 with a labyrinth-like internal structure extend parallel to one another, there being two in the present case, so that the medium to be subjected to a sterilizing effect can pass through the layers, in such a way that in their passage through the layers the medium is subjected to a large number of deflections. According to the invention, each layer consists of a material which is pervious to UV-radiation substantially without loss of intensity, that is, this radiation is not absorbed. A material having such a property is quartz. The layers 3,4 therefore preferably consist of quartz wool, in a suitable way, that is, in order to obtain the labyrinth structure, or laminated quartz paper or porous sintered quartz dust. It will be understood that the invention is not limited to the use of these materials, but that other materials can be employed, provided that they have the desired property of not absorbing UV radiation.

As illustrated, in the space 5 between the two layers 3,4, one or more UV-emitters 6 are provided, e.g. in the form of UV-tubes or UV-lamps, so that the two layers 3,4 are subjected to UV-radiation of substantially uniform intensity. The emitters 6 are so held in the housing 1 in a way known to an expert that a simple servicing or replacement possibility is given. If desired, the emitter can be embedded in the layers 3,4 or such an arrangement can be provided which is additional to that shown in FIG. 1.

In order to keep radiation losses at the side walls of the space 5 formed by the lateral frame members 2 as small as possible, it is further proposed in accordance with the invention that a reflector 7 is secured to the surfaces of the respective frame members 2 facing the space 5. These reflectors, as shown, have a dihedral cross-section, so that the UV-radiation impinging upon them is directed towards the layers 3,4.

In FIG. 1, the two layers 3,4 of non-UV-absorbent material are made in flat form, that is their surfaces lie in a plane. Practice has shown that layers formed for example of several superposed quartz wool mats can include regions in which direct or approximately direct through passages are given, which extend from one surface to the other. In such a region, the medium can therefore pass through the layers substantially without undergoing the necessary multiple deflections. In order to prevent such a free passage, the layers preferably have a substantially zig-zag-shaped arrangement, as is illustrated in connection with the second embodiment of the invention according to FIG. 2. The zig-zag-shaped arrangement of the layers 3,4 ensures that the medium passing through with the germs located therein always impinges at a certain, preferably an acute angle, on the surfaces of the layers 3,4, and therefore is subjected to deflections at these places. Moreover, by the zig-zag-shaped arrangement of the layers 3,4 the throughput cross-section, the germ-killing volume and the surface areas of the layers are substantially increased.

If desired, one layer, e.g. the upstream layer 4, can be of zig-zag-shape and the other, downstream layer 3 can be made flat.

Figure 2:
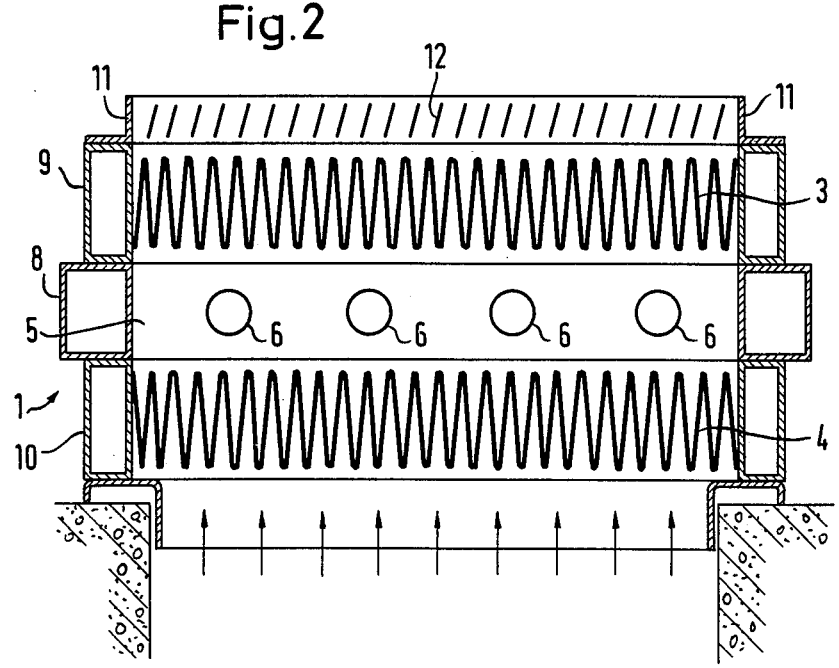
FIG. 2 shows a diagrammatic sectional view of a second embodiment of such a unit for a device according to the invention.

The embodiment of the invention according to FIG. 2 is different from the one previously described in that, apart from the zig-zag-shaped construction of the layers 3,4, it has a somewhat modified arrangement of the housing 1. As shown, a separate pair of spaced parallel lateral frame parts 8, 9, 10 with e.g. box-like cross-sections are provided for each layer 3,4 and for the UV-emitter 6. This offers the advantage that the separate components of the device can be made separately from one another and can be installed in the desired arrangement. For this purpose, the lateral frame parts 8, 9, 10 are so arranged that they can be readily assembled at the place of use of the device by means of screws, welding or the like so as to form the complete unit shown in FIG. 2. It will be understood that the lateral frame parts 8, 9, 10 can be made of any suitable material, such as metal or plastics material.

The embodiment of the invention shown in FIG. 2 is particularly suitable for use as an insert over the air outlet opening of an air-conditioning plant. As shown in FIG. 2, an angle member 11 is secured to each of the pair of lateral frame parts 9 which are located furthest away from the air outlet opening of the air-conditioning plant. Between the two angle members 11, a plate arrangement 12 extends which, on the one hand, distributes the effluent germ-free medium in a suitable manner into the space to be treated, e.g. an operating theatre, and on the other hand offers an effective radiation protection.

The devices shown in FIGS. 1 and 2 essentially have in common the purpose of killing the germs found in the medium by passage through the layers 3,4, but not to retain them in the manner of a filter. Since the germ-killing effect of the UV-radiation in a given radiation intensity is a function of the residence time for which the germs are exposed to the radiation, the layers 3,4 must be so constructed as to ensure that the germs undergo sufficiently frequent labyrinth-like deflections in their passage through the layers 3,4 that the desired residence time is produced. This is influenced on the one hand by the labyrinth structure of the layers 3,4 themselves and the other hand by their thickness and also their shape. With a zig-zag-shaped arrangement for the layers according to FIG. 2, particularly good results are achieved. Furthermore, the radiation intensity can be weakened by the deposition of foreign bodies, such as dust particles, in the layer 3,4 in the course of time. In order to be able to determine sufficiently early when such a weakening effect occurs, at a place in the device where for constructional or other grounds the radiation intensity is at its least or where the largest accumulation of foreign materials is likely to take place, a measuring probe (not shown) can be arranged which on detecting a prescribed limiting value for the radiation intensity actuates an alarm signal or, if required, automatically connects the device to a further supply of medium or air.

Figure 3:
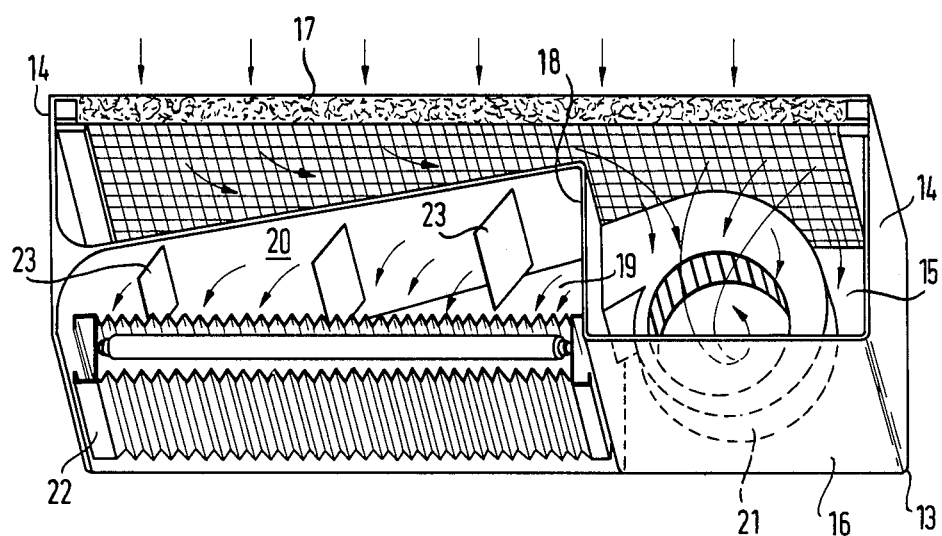
FIG. 3 shows a diagrammatic perspective view of a device according to the invention constructed as an air-circulating apparatus.

The device according to the invention is particularly suitable, though not exclusively, for air-circulation devices or for outlet devices for the air outlet apertures of air-conditioning plants. An air-circulating device constructed in accordance with the invention is illustrated in FIG. 3. This includes a housing indicated generally at 13, consisting of a pair of side walls 14, a front end wall which is described below in more detail, a rear end wall 17 formed of a conventional kind of pre-filtration material, a base wall 15 and a preferably removable cover (not shown). The rear end wall 17 constructed as a pre-filter has the purpose of filtering out the foreign materials, e.g. dust particles and the like, from the air entering the interior of the housing.

As shown, the front end wall consists of three preferably mutually integrally connected wall sections 16, 18, 20. The wall section 16 extends substantially parallel to the opposed end wall 17 and is directly connected with an end of the adjacent side wall 14. From the other end of the wall section 16, a second wall portion 18 extends substantially perpendicular to the direction of the rear end wall 17 and, at a suitable distance from the rear end wall 17, it terminates at and merges with the third wall section 20. The third wall section 20 extends from such end of the second wall section 18 in a substantially diagonal direction through the housing interior in the direction of the other side wall 14 and is formed integrally with or connected to this other inner surface at a distance from the front end edge of the side wall 14. By the wall sections 18,20, an enclosure 19 separate from the rest of the housing interior is formed, with a substantially saw-tooth-shaped plan.

In the second wall section 18, an opening is provided which is connected with the outlet duct of a pressure blower 21. The pressure blower is arranged in the region of the housing between the first wall section 16 and the rear end wall 17. By means of the pressure blower 21, air is sucked through the pre-filtering end wall 17, as shown by the arrow, and is forced into the enclosure 19. It then passes through the germ-killing device indicated generally at 22, which can have a construction for instance which is the same as that described in connection with FIG. 1. The germ-killing device 22 is located in the enclosure 19 in the region between a side wall 14 of the housing and the first wall section 16 so that it forms an extension of the wall section 16.

A uniform distribution of the air passing through the pressure blower 21 into the enclosure 19 upon the opposite surface of the device 22 is ensured, on the one hand, by the flow technique of the construction of the enclosure 19, as above described, and on the other hand by deflector plates 23, which are secured to the surface of the third wall section 20 facing the device 22 at suitable distances apart.

Figure 4:
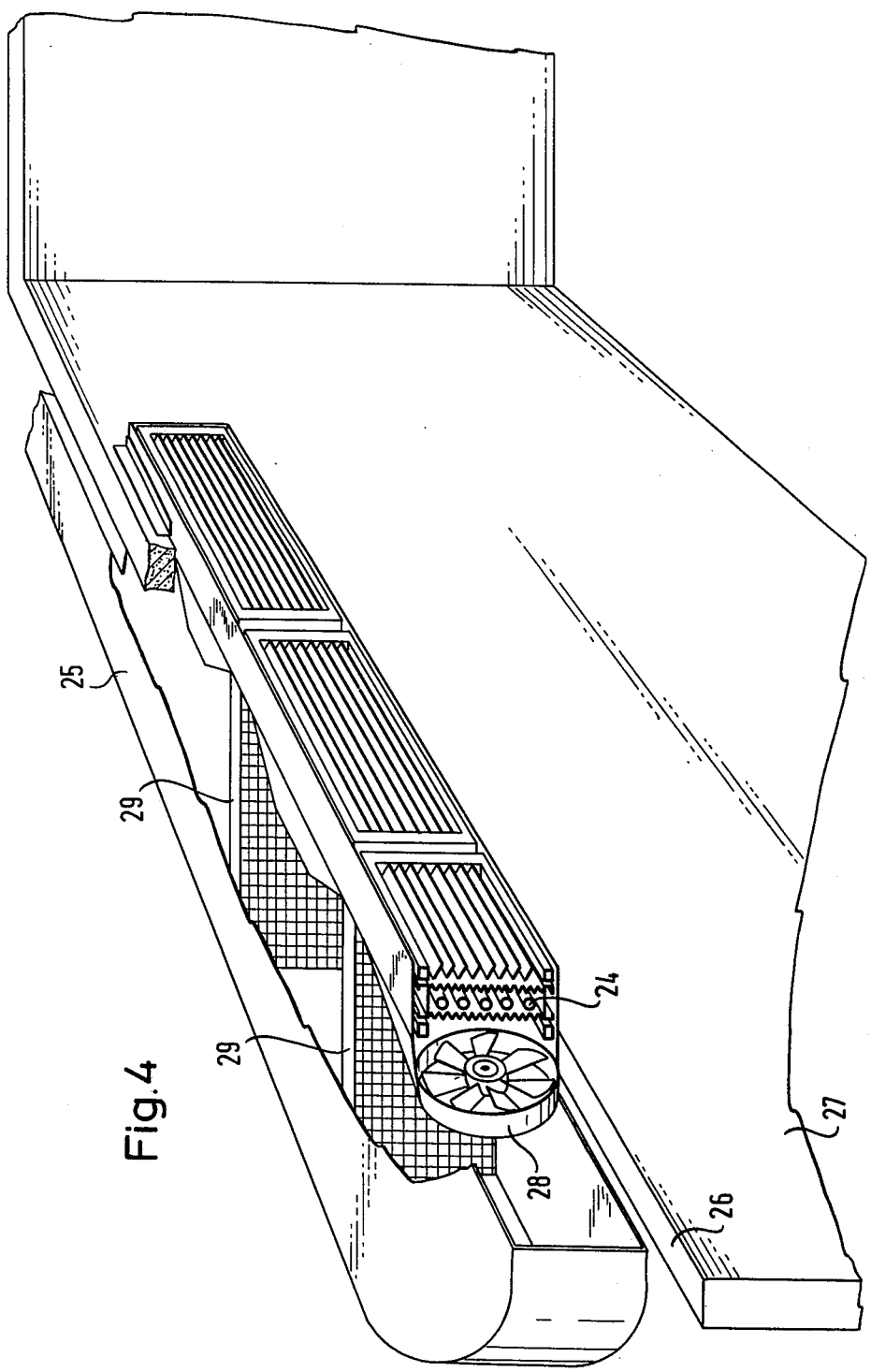
FIG. 4 shows a diagrammatic perspective partly broken-away view of a device according to the invention, illustrating its arrangement in an air outlet opening in the air duct of an air-conditioning plant.

FIG. 4 shows the construction of a germ-killing device according to the invention as an insert arrangement for an air outlet opening in the air duct of an air-conditioning plant. The construction of the germ-killing device 24 can correspond substantially to that described in connection with FIG. 2 so that the specific arrangements need not be described. The device 24 is thus secured in the way illustrated to the inside of an opening 26 in a structural wall 27. At the outer side of the structural wall 27 the air duct 25 extends, the air outlet opening of which (not shown) likewise is in connection with the aperture 26, so that air flowing through the duct 25 also passes through the device 24. As a rule, the static pressure in an air-conditioning plant is too low to be able to pass a satisfactory amount of air through the device 24. For this reason, in accordance with the invention, an additional pressure blower 28 is provided on the upstream or inlet side of the device 24 and is preferably combined with this in the form of a single construction unit, which acts as a pressure increasing stage. The pressure blower 28 can be further combined with a flow enclosure similar to the enclosure 29 according to FIG. 3. As shown, one or more pre-filters 29 of a conventional construction extend through the cross-section of the air duct 25 adjacent the outlet opening, in order to remove foreign materials, for example dust particles, from the air. Additional to or instead of the pre-filters 29, a filter wall similar to that shown in FIG. 3 can also be provided on the germ-killing insert device according to the invention.

Various preferred embodiments of the apparatus according to the invention have been described in detail above. It will be understood that various other means for providing modifications and alterations can be provided, as will be readily apparent to a man skilled in the art, without departing from the scope of the invention as defined in the appended claims.

What is claimed is:

1. An apparatus for carrying out the sterilization of gaseous media in which germs, bacteria and the like are contained, which comprises a housing, said housing holding therewithin (a) at least one layer of a filter-like material selected from the group consisting of quartz wool, quartz paper and sintered quartz dust, said material being non-absorbent of UV-radiation, whereby any incident UV-radiation passes substantially through said material, the said layer having such a labyrinth-like structure that the passage of germs through the layer is not substantially prevented, but is only substantially delayed, (b) at least one UV-emitter arranged to impinge UV-radiation upon the layer, and (c) a pressure blower for forcing through the layer the medium to be sterilized.

2. An apparatus according to claim 1, in which the UV-emitter is arranged in close proximity to the layer.

3. An apparatus according to claim 1, in which the layer is zig-zag shaped.

4. An apparatus according to claim 1, in which at least one further layer of said filter-like material is located in the housing substantially parallel to the one layer, and at least one UV-emitter is provided between the layers.

5. An apparatus according to claim 1, further comprising a pre-filter spaced upstream from said layer for removing dust and other impurities from the medium to be sterilized and a pressure blower disposed between said pre-filter and said layer of material non-absorbent of UV-radiation.

6. An apparatus according to claim 5, in which deflector plates are provided between said blower and said layer in order to distribute the medium emerging from the pressure blower substantially uniformly over the layer.

* * * * *